(12) United States Patent
Moser

(10) Patent No.: US 6,558,370 B2
(45) Date of Patent: May 6, 2003

(54) URINARY INCONTINENCE DEVICE

(75) Inventor: Julie Ann Moser, Lawrenceburg, IN (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 45 days.

(21) Appl. No.: 09/874,835

(22) Filed: Jun. 5, 2001

(65) Prior Publication Data

US 2002/0183711 A1 Dec. 5, 2002

(51) Int. Cl.[7] .............................. A61F 13/20; A61F 2/00
(52) U.S. Cl. ......................................... 604/904; 600/29
(58) Field of Search ..................... 604/385.17, 385.18, 604/904; 600/29–31; 606/191, 197

(56) References Cited

U.S. PATENT DOCUMENTS

| | | | |
|---|---|---|---|
| 1,280,979 A | 10/1918 | Ellis | |
| 1,790,801 A | 2/1931 | Dickstein | |
| 2,201,412 A | 5/1940 | Stein | |
| 2,487,200 A | 11/1949 | Trager | |
| 2,938,519 A | 5/1960 | Marco | |
| 3,079,921 A | 3/1963 | Brecht et al. | |
| 3,554,184 A | 1/1971 | Habib | |
| 3,572,341 A | * 3/1971 | Glassman | 128/285 |
| 3,643,661 A | 2/1972 | Crockford | |
| 3,646,929 A | 3/1972 | Bonnar | |
| 3,683,915 A | 8/1972 | Voss | |
| 3,706,311 A | 12/1972 | Kokx et al. | |
| 3,749,094 A | 7/1973 | Duncan | |
| 3,902,493 A | 9/1975 | Baier et al. | |
| 3,971,378 A | 7/1976 | Krantz | |
| 4,018,225 A | 4/1977 | Elmi | |

(List continued on next page.)

FOREIGN PATENT DOCUMENTS

| | | |
|---|---|---|
| DE | 804 835 | 7/1949 |
| DE | 3122954 A1 | 1/1983 |
| EP | 0 264 258 B1 | 4/1992 |
| EP | 0 363 421 B2 | 10/1995 |
| FR | 2 228 464 | 12/1974 |
| GB | 1115727 | 5/1968 |
| WO | WO 94/13223 A1 | 6/1994 |
| WO | WO 95/05790 A1 | 3/1995 |
| WO | WO 96/10965 A1 | 4/1996 |
| WO | WO 98/42281 A1 | 10/1998 |
| WO | WO 98/49980 A1 | 11/1998 |
| WO | WO 00/67662 A1 | 11/2000 |

OTHER PUBLICATIONS

Patent Cooperation Treaty Search Report from the International Search Authority, International Application No. PCT/US 02/08517 dated Jun. 21, 2002.

*Primary Examiner*—Dennis Ruhl
*Assistant Examiner*—C. Lynne Anderson
(74) *Attorney, Agent, or Firm*—Thomas J. Connelly

(57) ABSTRACT

A urinary incontinence device for alleviating female urinary incontinence is disclosed. The device includes a resilient member and a non-absorbent positioned adjacent to the resilient member. The non-absorbent is constructed from a fibrous material. The resilient member and the non-absorbent are rolled into a softwind having a first end, a second end, a first end diameter and a second end diameter. The resilient member is located adjacent to the second end of the softwind such that the second end diameter is larger than the first end diameter. The softwind is radially compressed into a pledget having an initial diameter, an insertion end, a trailing end and a uniform cross-sectional area therebetween. The insertion end is capable of expanding radially outward about 1.2 to about 10 times the initial diameter and the resilient member is capable of providing a supportive backdrop for a woman's urethra when inserted into a woman's vagina.

20 Claims, 5 Drawing Sheets

U.S. PATENT DOCUMENTS

| | | | |
|---|---|---|---|
| 4,019,498 A | 4/1977 | Hawtrey et al. | |
| 4,081,884 A | 4/1978 | Johst et al. | |
| 4,139,006 A | 2/1979 | Corey | |
| 4,212,301 A | 7/1980 | Johnson | |
| 4,266,546 A | 5/1981 | Roland et al. | |
| 4,307,716 A | 12/1981 | Davis | |
| 4,318,407 A | 3/1982 | Woon | |
| 4,328,804 A | 5/1982 | Shimatani | |
| 4,335,721 A | 6/1982 | Matthews | |
| 4,373,529 A | * 2/1983 | Lilaonitkul et al. | 128/285 |
| 4,467,806 A | 8/1984 | Bhiwandiwala et al. | |
| 4,668,557 A | 5/1987 | Lakes | |
| 4,875,898 A | 10/1989 | Eakin | |
| 5,041,077 A | 8/1991 | Kulick | |
| 5,045,079 A | 9/1991 | West | |
| 5,074,855 A | 12/1991 | Rosenbluth et al. | |
| 5,153,971 A | 10/1992 | Van Iten | |
| 5,336,208 A | 8/1994 | Rosenbluth et al. | |
| 5,352,182 A | 10/1994 | Kalb et al. | |
| 5,476,434 A | 12/1995 | Kalb et al. | |
| 5,483,976 A | 1/1996 | McLaughlin et al. | |
| 5,512,032 A | 4/1996 | Kulisz et al. | |
| 5,609,586 A | 3/1997 | Zadini et al. | |
| 5,611,768 A | 3/1997 | Tutrone, Jr. | |
| 5,659,934 A | 8/1997 | Jessup et al. | |
| 5,752,525 A | 5/1998 | Simon et al. | |
| 5,755,906 A | 5/1998 | Achter et al. | |
| 5,771,899 A | 6/1998 | Martelly et al. | |
| 5,785,640 A | 7/1998 | Kresch et al. | |
| 5,795,346 A | 8/1998 | Achter et al. | |
| 5,813,973 A | 9/1998 | Gloth | |
| 5,816,248 A | 10/1998 | Anderson et al. | |
| 5,885,204 A | 3/1999 | Vergano | |
| 5,908,379 A | 6/1999 | Schaefer et al. | |
| 5,988,169 A | 11/1999 | Anderson et al. | |
| 6,003,216 A | 12/1999 | Hull, Jr. et al. | |
| 6,013,023 A | 1/2000 | Klingenstein | |
| 6,030,375 A | 2/2000 | Anderson et al. | |
| 6,039,716 A | 3/2000 | Jessup et al. | |
| 6,039,828 A | 3/2000 | Achter et al. | |
| 6,090,038 A | 7/2000 | Zunker et al. | |
| 6,090,098 A | 7/2000 | Zunker et al. | |
| 6,142,928 A | 11/2000 | Zunker et al. | |
| 6,186,995 B1 | 2/2001 | Tharpe, Jr. | |
| 6,189,535 B1 | 2/2001 | Enhorning | |
| 6,299,573 B1 | 10/2001 | Hull, Jr. et al. | |

* cited by examiner

FORMING A RESILIENT MEMBER, A NON-ABSORBENT
AND A COVER

ALIGNING A SIDE EDGE OF SAID RESILIENT MEMBER
WITH A SIDE EDGE OF SAID NON-ABSORBENT

POSITIONING SAID NON-ABSORBENT ON SAID COVER
SUCH THAT SAID RESILIENT MEMBER IS
SPACED AWAY FROM SAID COVER

ROLLING SAID RESILIENT MEMBER, NON-ABSORBENT AND
SAID COVER INTO A SOFTWIND HAVING A NON-UNIFORM
CROSS-SECTIONAL CONFIGURATION

COMPRESSING SAID SOFTWIND INTO A PLEDGET
HAVING A UNIFORM CROSS-SECTIONAL CONFIGURATION

SECURING A WITHDRAWAL STRING TO SAID PLEDGET
TO FORM A UNINARY INCONTINENCE DEVICE

PLACING SAID UNINARY INCONTINENCE DEVICE
IN AN APPLICATOR

DISPENSING SAID UNINARY INCONTINENCE DEVICE
FROM SAID APPLICATOR INTO A WOMAN'S VAGINA

FIG. 11

URINARY INCONTINENCE DEVICE

FIELD OF THE INVENTION

This invention relates to a urinary incontinence device for alleviating female urinary incontinence and a method of making the same. More specifically, this invention relates to a urinary incontinence device for alleviating female urinary incontinence during episodes of increased intra-abdominal pressure.

BACKGROUND OF THE INVENTION

The primary etiological factor producing genuine stress urinary incontinence is the incomplete transmission of abdominal pressure to the proximal urethra due to displacement from its intra-abdominal position. Some women, especially women who have given birth to one or more children, and older women, can experience incidences of involuntary urine loss due to stress urinary incontinence or combined stress and urge incontinence. A sneeze or cough can increase the intra-abdominal pressure impinging on a person's bladder and cause the involuntary release of urine. The frequency and severity of such urine loss can increase as the muscles and tissues near the urethro-vaginal myofascial area grow weaker. It has also been recognized that the urinary sphincter muscle, which is located at the upper end of the urethra, adjacent to the bladder, works well at sealing off the passing of urine from the bladder to the urethra when it has a round or circular cross-sectional configuration. Support of the proximal urethra elevates it above the pelvic floor and subjects it to increases in intra-abdominal pressure, thus allowing compression and maintenance of continence. However, when this passageway becomes distorted into a cross-sectional configuration having more of an elliptical or oval appearance, the sphincter muscle can not close properly, therefore, the tendency for involuntary urine loss increases. One must remember that the urethra and vagina are not separate structures. Because of their common derivation from the urogenital sinus, they are fused in the distal two thirds of the urethra. In this region, they are bound together by the endopelvic connective tissue so that the support of the urethra depends not only on the attachments of the urethra itself to adjacent structures but also on the connection of the vagina and periurethral tissues to the pelvic wall.

As the world's female population ages, there is an ever-increasing need for a non-surgical method or measure to reduce the involuntary urine loss commonly associated with stress urinary incontinence. Today, there are a number of specialized products available for this purpose. Most of these products can only be purchased with a prescription and they need to be properly sized, physically inserted and/or adjusted by a medical doctor or a nurse practitioner in order for them to perform correctly. Few, if any, products are commercially available in the United States, without a prescription, to prevent involuntary urine loss from stress urinary incontinence.

In view of the lack of commercially available, non-prescription urinary incontinence prevention or mitigation devices, it is recognized that there is a need for a urinary incontinence device that can be purchased without a prescription. There is also a need for a urinary incontinence device that is uncomplicated and therefore more user friendly and can be managed by the consumer without the intervention of a medical practitioner. Furthermore, there is a need for a urinary incontinence device which is easy for women to insert into and remove from their bodies, be more comfortable to wear and provide psychological and realistic assurance that it is capable of properly performing over an extended period of time.

SUMMARY OF THE INVENTION

Briefly, this invention relates to a urinary incontinence device for alleviating female urinary incontinence. The urinary incontinence device includes a resilient member and a non-absorbent positioned adjacent to the resilient member. The non-absorbent is constructed from a fibrous material wherein the fibers do not absorb significant quantities of moisture within the fibers. The resilient member and the non-absorbent are rolled into an elongated softwind with the resilient member located adjacent to an end thereof. The softwind has a larger diameter at one end. The softwind is then radially compressed into an elongated pledget having an insertion end, a trailing end and a uniform cross-sectional area therebetween. The resilient member is capable of expanding the insertion end of the pledget to provide a supportive backdrop for a woman's urethra when inserted into a woman's vagina.

The general object of this invention is to provide a urinary incontinence device for alleviating female urinary incontinence. More specifically, this invention relates to a urinary incontinence device for alleviating female urinary incontinence during episodes of increased intra-abdominal pressure.

A more specific object of this invention is to provide a urinary incontinence device that is placed in a woman's vagina and provides support to a woman's urethra to prevent involuntary urine loss commonly associated with stress urinary incontinence.

Another object of this invention is to provide a urinary incontinence device that is simple to use, easy to insert and remove, and which is comfortable to wear.

A further object of this invention is to provide a urinary incontinence device that can be manufactured and sold for a reasonable cost.

Still another object of this invention is to provide a urinary incontinence device that can be purchased by a consumer without a prescription.

Still further, an object of this invention is to provide a urinary incontinence device that does not disrupt the availability of normal vaginal secretions, which are necessary for a healthy vaginal environment.

Other objects and advantages of the present invention will become more apparent to those skilled in the art in view of the following description and the accompanying drawings.

BRIEF DESCRIPTION OF THE DRAWINGS

FIG. 11 is a flow diagram of an alternative method of forming a urinary incontinence with a cover and housing the device in an applicator.

DETAILED DESCRIPTION OF THE PREFERRED EMBODIMENTS

Figure 1:
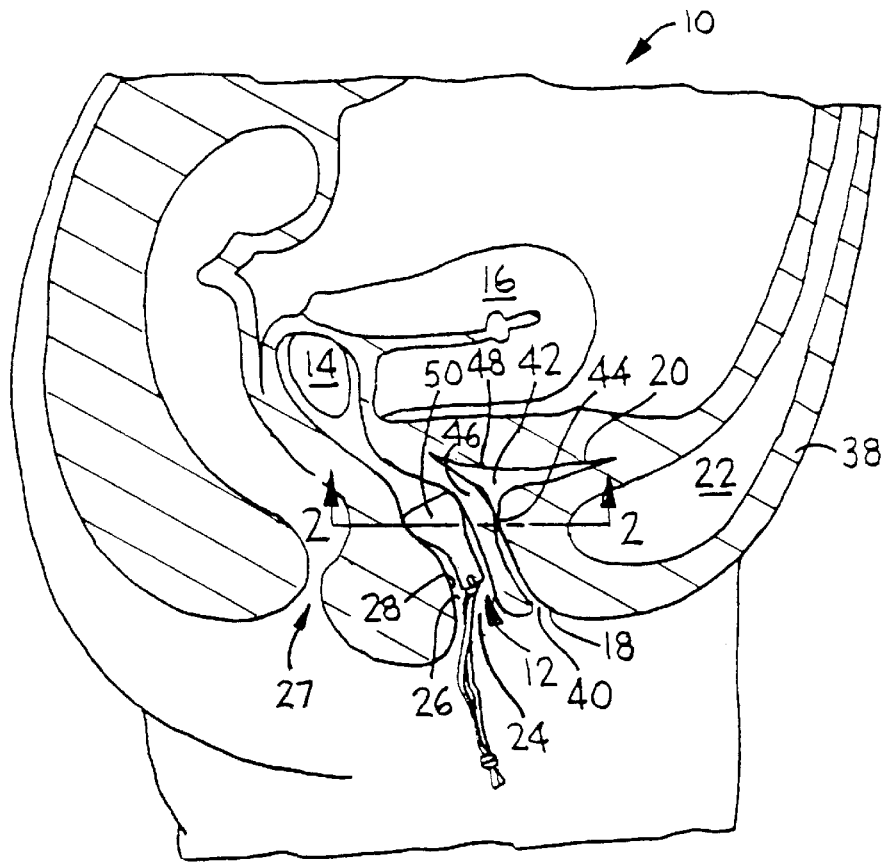
FIG. 1 is a mid-sagittal section of a human torso showing a urinary incontinence device positioned in the vaginal canal and cooperating with the symphysis pubis to allow the urethral tube to be compressed upon itself and alleviate urinary incontinence during episodes of increased intra-abdominal pressure.
Figure 2:
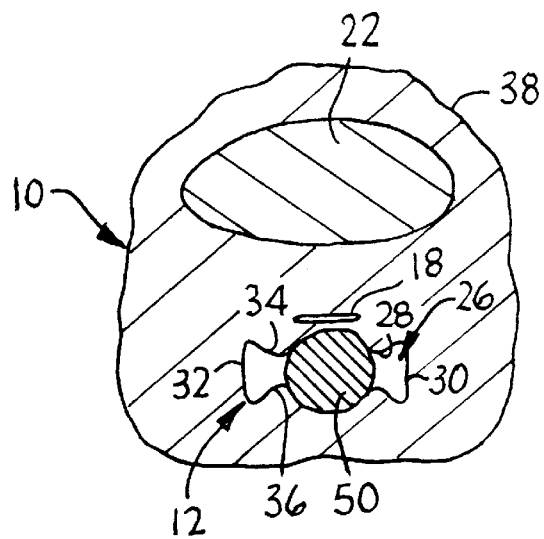
FIG. 2 is a sectional view taken along line 2—2 of FIG. 1 when the insertion end of the urinary incontinence device is in an expanded condition closing off the cross-section of the vaginal canal and providing a supportive backdrop for closing off the urethra.

Referring to FIGS. 1 and 2, a human torso 10 of a female is depicted showing the vagina 12, a cervix 14, a uterus 16, a urethra 18, a bladder 20 and a symphysis pubis 22. The vagina 12 has an introital opening 24 which exits the human body 10 and contains a vaginal canal 26 which extends from the introital opening 24 to the cervix 14. The vaginal canal 26 has a length which ranges from between about 4 inches to about 6 inches (about 102 millimeters (mm) to about 153 mm) in most woman. The cervix 14 is the entrance to the womb and is located between the upper aspect of the vaginal canal 26 and the uterus 16. A rectum 27 is located posterior to the vagina 12. The vaginal canal 26 has an inner periphery 28. The inner periphery 28 is made up of right and left lateral walls, 30 and 32 respectively, an anterior wall 34 and a posterior wall 36, see FIG. 2. The four walls 30, 32, 34 and 36 encompass the entire 360 degrees of the inner periphery 28. The anterior wall 34 is located closest to the urethra 18 and the urethra 18 is located between the symphysis pubis 22 and the vagina 12. The vaginal canal 26 can be divided into three approximately equal sections, each representing a third of the overall length. Each section is approximately 2 inches (approximately 51 mm) in length. The middle third of the vaginal canal 26 is the most important section for alleviating female urinary incontinence because of its proximity to the urethra 18 and is the location where a urinary incontinence device should be positioned. The middle third of the vaginal canal 26 also is horizontally offset from the symphysis pubis 22, which is a bony prominence situated adjacent to a front portion 38 of the human torso 10. Cooperation between a urinary incontinence device positioned in the middle third of the vagina 12 and the symphysis pubis 22 allows the urethra 18 to be compressed upon itself thereby alleviating involuntary urine flow from the bladder 20.

The urethra 18, also referred to as a urethral tube, is a hollow tube which extends from a first opening 40, which exits the human body 10, to a second opening 42 situated at the lower surface of the bladder 20. The urethra 18 has a length of about 1.5 inches (about 38 mm) in most women. The urethral 8 functions to discharge urine, which is temporarily stored in the bladder 20, from the human body. The urethra 18 has a plurality of urethral sphincter muscles 44 located along the length of its inner periphery. The urethral sphincter muscles 44 are situated below the opening 42 and are ringlike muscles that normally maintains constriction of the urethra 18 to prevent the passage of urine therethrough. The relaxation of the urethral sphincter muscles 44 by normal physiological functioning will permit urine to be voluntarily expelled from the human body.

Still referring to FIG. 1, the human torso 10 further includes musculature and body tissue located in the urethro-vaginal myofascial area 46 which is situated between the vagina 12 and the symphysis pubis 22. The bladder 20 lies posterior to the symphysis pubis 22 and is separated from the rectum 27 by the vagina 12 and the uterus 16. The ureters (not shown), which transport urine from the kidneys to the bladder 20, pass from the pelvis to the posterior aspect of the urinary bladder 20. The fundus vesicae 48, into which both of the ureters terminate, is located adjacent to the anterior wall 34 of the vagina 12.

Referring to FIGS. 1–2, a urinary incontinence device 50 is shown positioned in the middle third of the length of the vaginal canal 26. The urinary incontinence device 50 is designed to bridge across the vagina 12 and supports the musculature and body tissue located in the urethro-vaginal myofascial area 46. In FIG. 2, the urinary incontinence device 50 is shown in an expanded state wherein the resilient portion of the urinary incontinence device 50 has expanded outward toward its original shape. In the expanded state, the insertion end of the urinary incontinence device 50 has a greater diameter and occupies an overall larger cross-sectional area than the narrow end. The insertion end of the urinary incontinence device 50 extends radially outward and is in intimate contacts with the entire inner periphery of the vaginal canal 26. In other words, a portion of the urinary incontinence device 50 is directly touching all four interior walls 30, 32, 34 and 36 of the vaginal canal 26 and is providing a supportive backdrop for the urethral tube 18. The urethral tube 18 is now compressed sufficiently to intercept the flow of urine and thereby provides support to the urinary sphincter muscle 44 so that it can function properly. By permitting the urethral tube 18 to be compressed upon itself between the urinary incontinence device 50 and the symphysis pubis 22, one can limit the involuntary flow of urine from the bladder 20.

Figure 3:
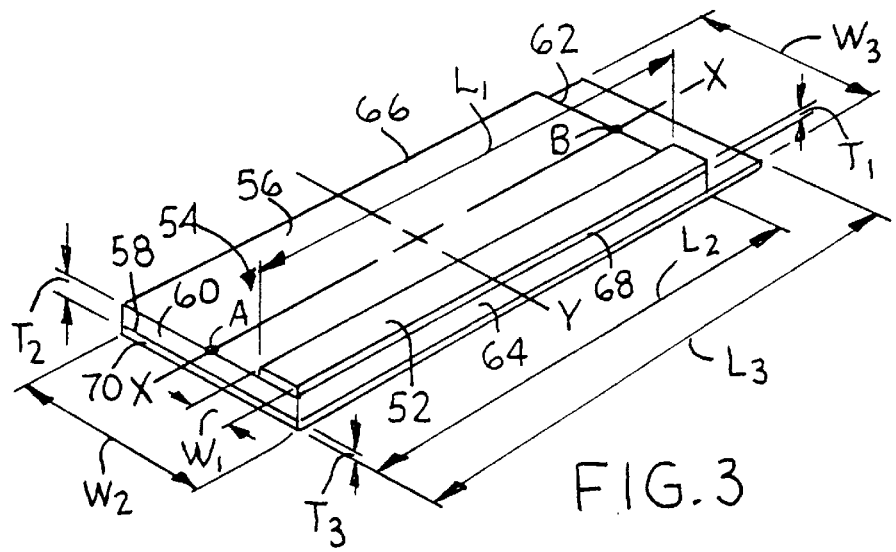
FIG. 3 is a perspective view of a cover, a non-absorbent and a resilient member shown in a flat orientation before being rolled and compressed to form a urinary incontinence device.
Figure 4:
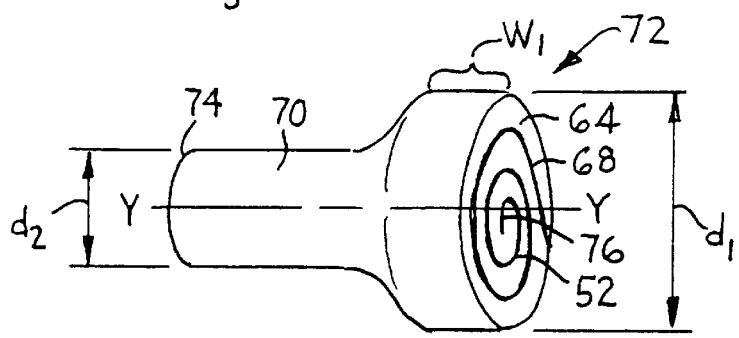
FIG. 4 is a perspective view of the three layers depicted in FIG. 3 after being rolled up along the longitudinal axis X—X to form an elongated softwind having an enlarged end.
Figure 5:
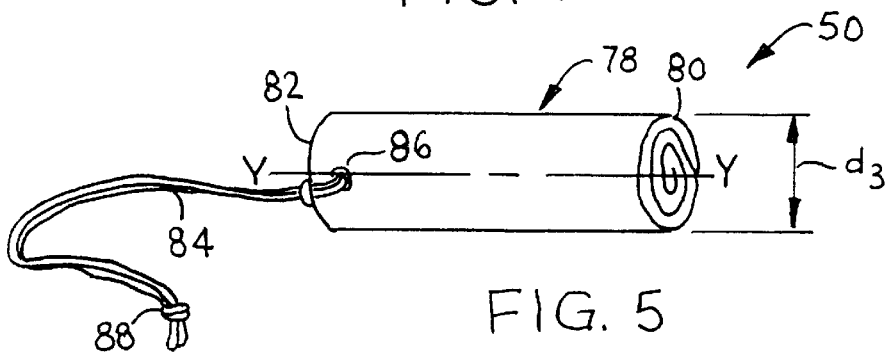
FIG. 5 is a perspective view of an elongated pledget having an insertion end, a trailing end and a uniform cross-sectional area therebetween that is formed by compressing the softwind shown in FIG. 4.

Referring now to FIGS. 3–5, the urinary incontinence device 50 includes a resilient member 52 and a non-absorbent 54. The resilient member 52 can be a natural or synthetic material that has the ability to quickly recover or return to approximately its original shape and/or dimension once it is placed into a woman's vagina 12. While residing within a woman's vagina 12, the resilient member 52 can contract temporarily by changes in the intra-abdominal pressure as a result of laughing, sneezing, coughing, or the like. A resilient material is a material that can return to or resume its original shape or position after being bent, stretched or compressed. The resilient member 52 should also exhibit elasticity and flexibility so that it can be stretched or compressed and still retain the capability of returning to approximately its original shape.

Two natural materials from which the resilient member 52 can be formed include natural rubber and wool. The number of synthetic materials from which the resilient member 52 can be formed is much greater. Synthetic materials that can be used include polyolefins, polyurethanes, polyethylene oxide (PEO), polyvinyl alcohol (PVA), as well as blends thereof. The resilient member 52 can also be formed from resilient fibers constructed from polyolefin-based fibers, polyethylene oxide fibers, hydrophobic rayon fibers and the like. Such fibers should preferably have characteristics similar to those of resilient foams. The resilient fibers can be formed from twisted, curled or cross-linked cellulose fibers or from a mixture thereof. Furthermore, the resilient member 52 can be formed from a resilient foam. The resilient foam can be an open cell or a closed cell foam.

The resilient member 52 can also be made from a wettable foam. An open cell wettable foam that works well and has good resilient properties is commercially available under the trademark ACQUELL®. "ACQUELL" is sold by Sentinel Products Corporation, which has an office at 70 Airport Road, Hyannis, Mass. 02601. A polyethylene closed cell wettable foam having good flexibility characteristics also works well. This foam is commercially sold under the trademark VOLARA®. "VOLARA" is available from Voltex, a Division of Sekisui America Corporation, having an office at 100 Shepard Street, Lawrence, Mass. 01843.

The resilient member 52 should also be capable of having what is known as "dry and wet" expansion characteristics. In other words, the resilient member 52 should be made from a material that is capable of expanding or contracting back to or towards its original configuration in a dry state, a wet state or in a semi dry-wet state. Dry expansion of the urinary incontinence device 50 is beneficial in that the device does not have to be wetted by body fluids before the resilient member 52 is capable of expanding within a woman's vagina 12.

In FIG. 3, the resilient member 52 is depicted as a relatively long narrow strip of material being rectangular in cross-section. However, the resilient member 52 can have a square, circular, oval or any other cross-sectional configuration, if desired. The resilient member 52 is shown having a length $L_1$, a width $W_1$ and a thickness $T_1$ The width $W_1$ and the thickness $T_1$ can remain constant over the entire length $L_1$. If desired, the dimensions of the resilient member 52 can vary so that the resilient member 52 has a non-uniform cross-section along its length $L_1$. The length $L_1$ of the resilient member 52 can be equal to or less than the length of the non-absorbent 54.

In the embodiment shown in FIG. 3, the length $L_1$ of the resilient member 52 can range from between about 3 inches (about 76 mm) to about 8 inches (about 203 mm). Preferably, the length $L_1$ of the resilient member 52 will be from between about 4 inches (about 102 mm) to about 6 inches (about 152 mm). Most preferably, the length $L_1$ of the resilient member 52 will be about 5 inches (about 127 mm). The width $W_1$ of the resilient member 52 can range from between about 0.12 inches (about 3 mm) to about 1 inch (about 25 mm). Preferably, the width $W_1$ of the resilient member 52 will be from between about 0.25 inches (about 6.4 mm) to about 0.5 inches (about 12.7 mm). Most preferably, the width $W_1$ of the resilient member 52 will be about 0.375 inches (about 9.5 mm). The thickness $T_1$ of the resilient member 52 can range from between about 0.1 inch (about 2.5 mm) to about 0.5 inches (about 12.7 mm). Preferably, the thickness $T_1$ of the resilient member 52 will be from between about 0.1 inches (about 2.5 mm) to about 0.4 inches (about 10 mm). Most preferably, the thickness $T_1$ of the resilient member 52 will be less than about 0.3 inches (about 7.6 mm).

When the resilient member 52 has a round or circular cross-sectional configuration, the diameter can range from between about 0.1 inch (about 2.5 mm) to about 1.125 inches (about 27.5 mm). Preferably, the diameter of the resilient member 52 will be from about 0.1 inch (about 2.5 mm) to about 0.5 inches (about 12.7 mm). Most preferably, the diameter of the resilient member 52 will be less than about 0.3 inches (about 7.6 mm). For odd cross-sectional shapes, like an oval, a bi-lobal, a tri-lobal, an ellipse, etc. the larger dimension should be no greater than about 1.125 inch (about 27.5 mm).

Referring again to FIG. 3., the non-absorbent 54 is shown having a first surface 56, a second surface 58, a first end 60, a second end 62, a first side edge 64 and a second side edge 66. The non-absorbent 54 also has a central longitudinal central axis x—x and a central transverse axis y—y. The resilient member 52 is positioned adjacent to the first surface 56 of the non-absorbent 54. Preferably, resilient member 52 is positioned parallel to and spaced away from the central longitudinal axis x—x. As depicted in FIG. 3, the resilient member 52 has a longitudinal side edge 68 and is positioned on the first surface 56 such that its side edge 68 is aligned coterminuous with the first side edge 64 of the non-absorbent 54. This arrangement allows the resilient member 52 to be located approximate one end of the finished urinary incontinence device 50.

The non-absorbent 54 has a length $L_2$ that is equal to or greater than the length $L_1$ of the resilient member 52. In addition, the non-absorbent 54 has a width $W_2$ that ranges from between about one to about eight times the width $W_1$ of the resilient member 52. Preferably, the width $W_2$ of the non-absorbent 54 will be from between about two to about four times the width $W_1$ of the resilient member 52. Most preferably, the width $W_2$ of the non-absorbent 54 is about three times the width $W_1$ of the resilient member 52. The non-absorbent 54 has a thickness $T_2$ that can be less than, equal to or be greater than the thickness $T_1$ of the resilient member 52. It should be noted that the non-absorbent 54 can be a single ply of material or it can be constructed of two or more plies, such as a laminate.

The non-absorbent 54 is constructed from materials that exhibit little, and preferably no, absorbent characteristics. The non-absorbent 54 differs from a catamenial tampon in that it does not function to absorb body fluid. Instead, the non-absorbent 54 is designed to bridge across the vagina 12 and support the musculature and body tissue located in the urethro-vaginal myofascial area 46. The urethra 18 can be compressed upon itself sufficiently to interrupt the flow of urine and doing so can provide support to the urinary sphincter muscles 44 so that they can function properly.

For purposes of this invention, a non-absorbent is defined as a material wherein the fibers do not absorb significant quantities of moisture within the fibers themselves. It is to be recognized that virtually all materials will absorb some small quantity of moisture. A fiber is considered to be non-absorbent for present purposes if it will intrinsically gain no more than about 6 percent in weight when a bone-dry fiber is maintained at 21 degrees Celsius and at 65 percent relative humidity for 24 hours. Non-absorbent materials include but are not limited to nylons, rayons, spun cellulose, LYCRA®, KEVLAR®, carbon fibers and the like. "LYCRA" and "KELVAR" are trademarks of E. I. DuPont de Nemours & Company having an office at 1007 Market Street, Wilmington, Del. 19801. The non-absorbent 54 can also be formed from a web made from bicomponent fibers which are commercially available from Chisso Corporation having an office at 1411 Broadway, 35$^{th}$ floor, New York, N.Y. Such fibers are sold under the name "Chisso ESC Bicomponent Fiber" and consist of a polypropylene core surrounded by a polyethylene sheath. Fibers that work well have a denier of about 3 and are about 38 millimeters in length. Other bicomponent fibers made from polypropylene, polyethylene, etc. are commercially available from suppliers such as Exxon and Dow Chemical, as well as from other vendors.

Alternatively, the non-absorbent 54 could be an absorbent material such as a cotton/rayon blend that has been chemically treated with a surfactant to make it non-absorbent. However, materials comprised of truly non-absorbent fibers work best.

Referring again to FIG. 3, the second surface 58 of the non-absorbent 54 is shown being positioned adjacent to a cover 70. The cover 70 is an optional element and need not be present to form the urinary incontinence device 50. However, the cover 70 can provide a smooth outer surface that may or may not be chemically treated to facilitate a comfortable insertion and/or removal into and out of a woman's vagina. When present, the cover 70 has a length $L_3$ that is equal to or greater than the length $L_2$ of the non-absorbent 54. When the length $L_3$ of the cover 70 is longer than the length $L_2$ of the non-absorbent 54, it allows the cover 70 to overlap upon itself once the three layers 52, 54 and 70 are rolled up into a cylindrical form. The extra length $L_3$ of the cover 70 facilitates bonding of the cover 70 to itself by heat, pressure, a combination of heat and pressure, or by some other conventional means known to those skilled in the art. If the cover 70 is formed from a material that does not readily bond to itself, an adhesive, glue or other bonding or fastening medium can be used.

The cover 70 also has a width $W_3$ that can be less than, equal to or greater than the width $W_2$ of the non-absorbent 54. Preferably, the width $W_3$ of the cover 70 is approximately equal to the width $W_2$ of the non-absorbent 54. This configuration allows the ends of the urinary incontinence device 50 to be exposed. The cover 70 also has a thickness $T_3$ that is less than about 0.3 inches (about 7.6 mm). Preferably, the thickness $T_3$ of the cover 70 should be less than about 0.2 inches (about 5 mm), and most preferably, the thickness $T_3$ is less than about 0.1 inches (about 2.5 mm).

The cover 70 can be either liquid permeable or liquid-impermeable. Preferably, the cover 70 is liquid-impermeable. By "liquid-permeable" it is meant that body fluid is able to pass through the cover 70 in a quick and efficient manner. The cover 70 can be hydrophilic, hydrophobic or a combination of each. By "hydrophilic" it is meant that the cover 70 has an affinity for absorbing or tending to combine with water. By "hydrophobic" it is meant that the cover 70 is antagonistic to or tends not to combine with water. The cover 70 can also be treated with a surfactant or some other chemical to make it hydrophilic, hydrophobic or to make it more hydrophilic or more hydrophobic. Surfactants having high lubricity and hydrophobicity and which are non-irritating to the vaginal mucosa are preferred since they discourage the attraction, accumulation and retention of any resident vaginal fluid.

When the cover 70 is liquid-impermeable, it serves to block body fluid from contacting the non-absorbent 54. Since the non-absorbent 54 is not designed to absorb any body fluid, it is not necessary that the cover 70 be liquid-impermeable.

Liquid permeable materials include woven and nonwoven materials having a porous substrate. Woven materials include textile fabrics that can be made from rayon, cotton or polyolefins. The polyolefins can be either staple or continuous filaments. The nonwoven materials can include spunbond, bonded-carded webs and hydroentangled webs. One material that works well as a cover is a 0.4 ounces per square yard (osy) spunbond polypropylene having a crepe of at least 30 percent. Another material that works well as a cover is a 0.6 osy spunbond polypropylene having a crepe of at least 30 percent. Spunbond and bonded-carded webs are commercially available from Kimberly-Clark Corporation having an office at 401 N. Lake Street, Neenah, Wis. 54956. Another nonwoven material that can be used as the cover 70 is formed from 100 percent polyester fibers held together by a binder. This material is known as power-bonded-carded web (PBCW). PBCW is commercially available from HDK Industries, Inc. having an office at 304 Arcadia Drive, Greenville, S.C. 29609.

The cover 70 can also be constructed from a liquid-impermeable material. A good liquid-impermeable material is a micro-embossed, polymeric film, such as polyethylene or polypropylene. Bicomponent films can also be used. A preferred liquid-impermeable material is polyethylene film. The cover 70 can further be formed from an apertured thermoplastic film having either a two or three-dimensional thickness. Apertured thermoplastic films are available from several commercial vendors. One such vendor is Pantex srl, Pantex Sud srl, Via Terracini snc, having an office at 51031 Agliana, Pistoia, Italy. A second vendor is Applied Extrusion Technology having a mailing address of P.O. Box 582, Middleton, Del. 19709.

The cover 70 can also be treated with an aqueous solution to reduce frictional drag, to give the urinary incontinence device 50 a permanent wettability and/or to enhance the ease of insertion into and removal from a woman's vagina.

Referring now to FIGS. 3–5, the resilient member 52, the non-absorbent 54 and the cover 70 are rolled up or radially wound along the central longitudinal axis x—x into an elongated softwind 72. The non-absorbent 54, shown in FIG. 3, has points A and B located at the first and second ends, 60 and 62 respectively. Preferably, the three layers 52, 54 and 70 are rolled or radially wound perpendicular to the x—x axis starting at point A and terminating at point B. The extra length of the cover 70, located adjacent to point B and extending outward therefrom, allows the cover 70 to wrap upon itself and provides the softwind 72 with a smooth finished appearance. The softwind 72 has a first end 74 and a second end 76 and possesses a non-uniform configuration between the first and second ends, 74 and 76 respectively. The resilient member 52 is located adjacent to the second end 76 and this causes the second end 76 to have a diameter $d_1$ that is larger than the diameter $d_2$ of the first end 74. This larger diameter $d_1$ extends back toward the first end 74 a distance approximately equal to the width $W_1$ of the resilient member 52.

Referring to FIG. 5, the softwind 72 is then radially compressed along the central transverse axis y—y into an elongated pledget 78 having a generally cylindrical configuration. The pledget 78 has an insertion end 80, a trailing end 82 and a uniform cross-sectional area therebetween. The pledget 78 has a diameter $d_3$ that is generally smaller than the diameter $d_2$ of the second end 74 of the softwind 72. The diameter $d_3$ can range from between about 0.2 inches (about 5 mm) to about 2 inches (about 51 mm). Preferably, the diameter $d_3$ of the pledget 78 will be from about 0.5 inches (about 12.7 mm) to about 1 inch (about 25.4 mm). Most preferably, the diameter $d_3$ of the pledget 78 is less than about 0.75 inches (about 19 mm).

A withdrawal means 84, preferably in the form of an elongated string or ribbon is securely attached to the pledget 78. The withdrawal string 84 facilitates the removal of the urinary incontinence device 50 from the vaginal canal 26. When the user is ready to remove the urinary incontinence device 50, she will pull downward on the withdrawal string 84. This action will cause the urinary incontinence device 50 to be comfortably withdrawn from the vaginal canal 26.

One way of securing the withdrawal string 84 to the pledget 78 is to form an aperture 86 transversely through the pledget 78 near the trailing end 82. Preferably, the aperture 86 is spaced a short distance from the trailing end 82. The aperture 86 can be located a distance of from between about 0.1 inches (about 2.5 mm) to about 0.5 inches (about 12.7 mm) from the trailing end 82. Although the aperture 86 can be located almost anywhere in the pledget 78, it preferably is located about 0.25 inches (about 6.4 mm) from the trailing end 82. The aperture 86 can be formed with a needle, an awl or some other type of piercing device known to those skilled in the art. The withdrawal string 84 is then passed through the aperture 86. The withdrawal string 84 can be looped upon itself to form a secure attachment. The free ends of the withdrawal string 84 are then tied in a knot 88 to assure that the withdrawal string 84 will not separate from the urinary incontinence device 50. The knot 88 also serves to prevent fraying of the withdrawal string 84 and to provide a place or point where a woman can grasp the withdrawal string 84 when she is ready to remove the urinary incontinence device 50 from her vagina 12. The compressed pledget 78 with the withdrawal string 84 attached constitutes the finished urinary incontinence device 50.

The withdrawal string 84 can be constructed from various types of threads or ribbons. A thread or ribbon made from 100 percent cotton fibers works well. The withdrawal string 84 should have a length which extends beyond the trailing end 82 of the pledget 78 from between about 2 inches (about 51 mm) to about 8 inches (about 203 mm). Preferably, the withdrawal string 84 should have a length which extends beyond the trailing end 82 from between about 4 inches (about 102 mm) to about 6 inches (about 152 mm), and most preferably, by about 5 inches (about 127 mm). The withdrawal string 84 can be dyed and/or treated with an anti-wicking agent, such as wax, before being secured to the urinary incontinence device 50. The anti-wicking agent will reduce and hopefully prevent body fluids from wicking along the withdrawal string 84 and contacting the inner surface of a woman's undergarment. A dry, clean withdrawal string 84 is preferred by the user, especially when she goes to remove the urinary incontinence device 50 from her vagina 12.

The insertion end 80 of the urinary incontinence device 50 is designed to be the first part to enter a woman's vagina 12. When properly inserted into the vagina 12, the entire urinary incontinence device 50 will be positioned in approximately the middle third of the length of the vaginal canal 26. In other words, the urinary incontinence device 50 occupies approximately the middle 2 inches (about 51 mm) of the vaginal canal 26 and provides a supportive backdrop for the body tissue and muscles located in the urethro-vaginal myofascial area 46. In this position, the urinary incontinence device 50 will be aligned with the upper portion of the urethra 18 and will provide a supportive backdrop for at least half of the urethra 18. During episodes of increased intra-abdominal pressure, the compression that occurs to the urethro-vaginal myofascial area 46 between the symphysis pubis 22 and the urinary incontinence device 50 allows the sphincter muscles 44 to acquire a more normal configuration. The sphincter muscles 44 can then operate properly and the urethral 8 is capable of being compressed upon itself. These two functions assist one another in alleviating involuntary urine flow from the bladder 20.

The insertion end 80 of the urinary incontinence device 50 is capable of expanding radially outward. It is the expansion in the radial direction that is the most important for this invention. The insertion end 80 can be designed to radially expand outward from between about 1.2 to about 10 times the initial diameter $d_3$ of the pledget 78. Preferably, the insertion end 80 will be capable of radially expanding outward from between about 1.5 to about 4 times the initial diameter $d_3$ of the pledget 78. More preferably, the insertion end 80 will be capable of radially expanding outward at least 2 times the diameter $d_3$ of the pledget 78. The maximum amount of radial expansion of the insertion end 80 will depend on a number of factors, including the size, shape, location and composition of the resilient member 52, as well as the thickness and inherent properties of the non-absorbent 54 and the cover 70. It is envisioned that one could design the urinary incontinence device 50 such that the insertion end 80 could radially expand more than 10 times the initial diameter $d_3$ of the pledget 78, if desired.

The urinary incontinent device 50 will retain its generally compressed cylindrical shape until it is positioned within the vagina 12. To assist the urinary incontinent device 50 in retaining its compressed shape, it can be housed in an applicator or be wrapped in a thermoplastic wrapper.

It should be noted that when the urinary incontinence device 50 is properly positioned in the vagina 12, only the withdrawal string 84 will be exposed and extend outward from the introital opening 24.

Figure 6:
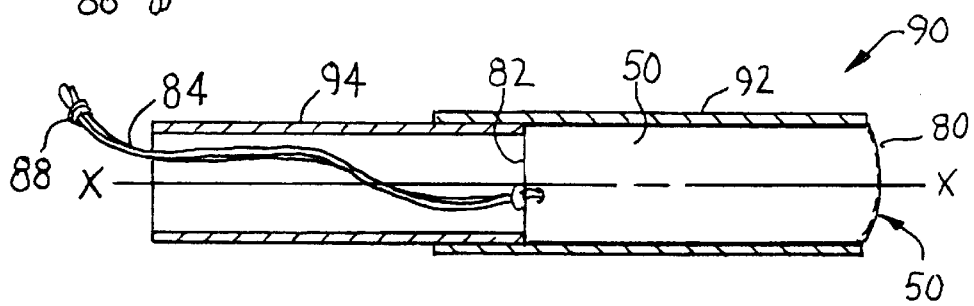
FIG. 6 is a side view of the pledget housed in an applicator.

Referring now to FIG. 6, the urinary incontinence device 50 is shown retained or housed in an applicator 90. The applicator 90 will facilitate insertion of the urinary incontinence device 50 into a woman's vagina 12 and will assist in maintaining the uniform cross-sectional area of the pledget 78 until it is inserted into a woman's vagina. The applicator 90 can be identical to a tampon applicator, if desired. The applicator 90 is depicted as a two-piece telescoping applicator having a hollow outer tube 92 and a hollow inner tube 94. The urinary incontinence device 50 is positioned within the outer tube 92 such that the inner tube 94, which has a smaller diameter, can be pushed against the trailing end 82. This action will cause the urinary incontinence device 50 to be expelled from the outer tube 92. The applicator 90 can be constructed of paper, cardboard or plastic. One example of an applicator is taught in U.S. Pat. No. 5,795,346 which issued to Achter et al. on Aug. 18, 1998 and is entitled: "TAMPON HAVING A RESILIENT MEMBER."

It should be recognized that the urinary incontinence device 50 could also be digitally inserted into a woman's vagina 12. For digital insertion, a woman would use one of her fingers to push on the trailing end 82 of the urinary incontinence device 50 so that the insertion end 80 could easily enter her vagina. With digital insertion, there would be no need for an applicator.

Figure 7:
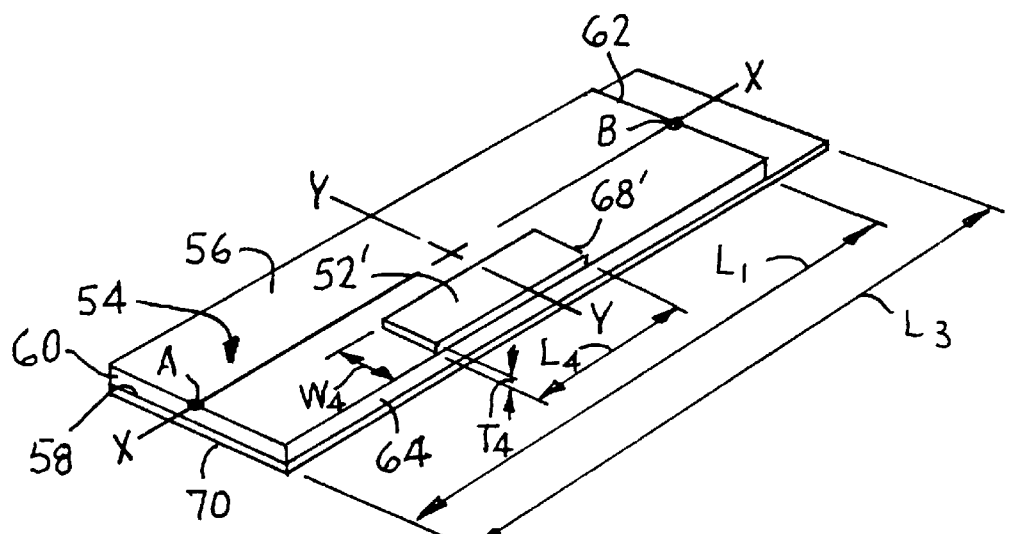
FIG. 7 is a perspective view of an alternative embodiment of a cover, a non-absorbent and a relatively short resilient member shown in a flat orientation before being rolled and compressed to form a urinary incontinence device.
Figure 8:
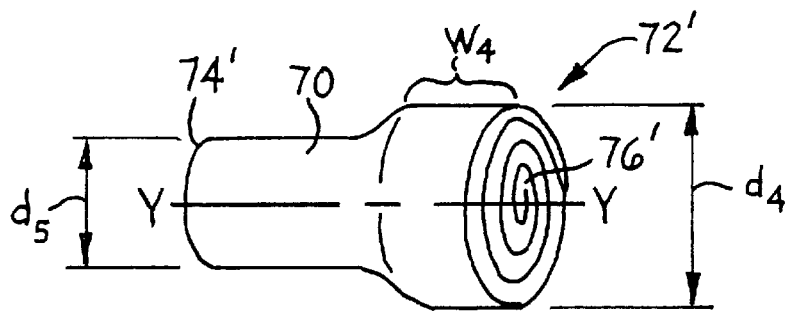
FIG. 8 is a perspective view of the three layers depicted in FIG. 7 after being rolled up along the longitudinal axis X—X to form an elongated softwind having an enlarged end.
Figure 9:
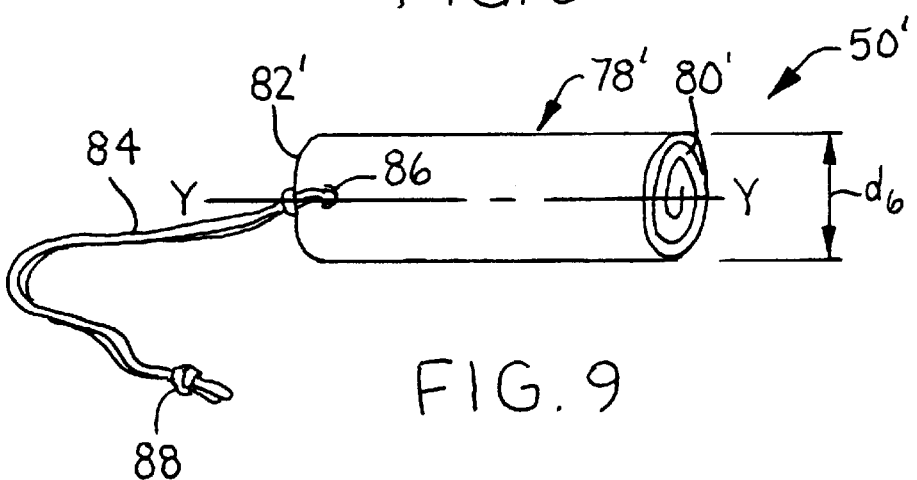
FIG. 9 is a perspective view of an elongated pledget having an insertion end, a trailing end and a uniform cross-sectional area therebetween that is formed by compressing the softwind shown in FIG. 8.

Referring now to FIGS. 7–9, an alternative embodiment of a urinary incontinence device 50' is depicted. For the purpose of clarity, the numerals recited in FIGS. 3–5 will be used for this embodiment except that prime numbers will be used for new elements. The resilient member 52' is depicted as a member having a length $L_4$, a width $W_4$ and a thickness $T_4$. The length $L_4$ of the resilient member 52' is smaller than the length $L_2$ of the resilient member 52 by at least 50%. Preferably, the length $L_4$ of the resilient member 52' is less than about 35% of the length $L_2$ of the resilient member 52. The width $W_4$ of the resilient member 52' is greater than the width $W_2$ of the resilient member 52. The width $W_4$ of the resilient member 52' is about twice the width $W_2$ of the resilient member 52. The thickness $T_4$ of the resilient member 52' is about equal to the thickness $T_2$ of the resilient member 52.

The resilient member 52' is positioned so as to straddle the central transverse axis y—y. However, it should be noted that the resilient member 52' could be aligned adjacent to or near either the first end 60 or the second ends 62. By aligning the resilient member 52' closer to one of the first or second ends, 60 or 62 respectively, the position of the resilient member 52' in the rolled up softwind 72' will change. For example, if the resilient member 52' is placed adjacent to the first end 60 and the softwind 72' is rolled up starting from point A, the resilient member 52' will be located next to the center of the softwind 72'. This location may make it more difficult for the resilient member 52' to radially expand outward. On the other hand, if the resilient member 52' is placed adjacent to the second end 62 and the softwind 72' was rolled up starting again at point A, the resilient member 52' will be located near the outer periphery of the softwind 72'. In this position, the resilient member 52' could more easily expand radially outward.

Besides having a shorter length $L_4$ than the resilient member 52, the resilient member 52' also differs from that shown in FIG. 3 in that it has a greater width $W_4$. This increase in width $W_4$ will enlarge the expansion area of the urinary incontinence device 50'. This enlarged expansion area, denoted by $W_4$ in FIG. 8, is beneficial for a number of reasons. First, the urinary incontinence device 50' can be inserted farther up the vaginal canal 26 while still being able to function as a support for the urethro-vaginal myofascial area 46. Second, the enlarged dimension $W_4$ will contact a greater surface area of the inner periphery 28 of the vaginal canal 26 and can therefore operate over a longer axial dimension. Third, by using the larger area of expansion, the urinary incontinence device 50' may be more comfortable for a woman to use when properly placed in her vagina 12.

Referring to FIGS. 8 and 9, one will notice that as the resilient member 52', the non-absorbent 54 and the cover 70, are rolled up or radially wound along the central longitudinal axis x—x, to form a softwind 72'. The softwind 72' has a greater area of expansion, denoted by the dimension $W_4$. The softwind 72' has a first end 74' and a second end 76' and possesses a non-uniform cross-section therebetween. The resilient member 52' is located adjacent to the second end 76' of the softwind 72' and this causes the second end 76' to have a diameter $d_4$ that is larger than the diameter $d_5$ of the first end 74'. This larger diameter $d_4$ extends back toward the first end 74' a distance approximately equal to the width $W_4$ of the resilient member 52'.

The softwind 72' is then radially compressed along the central transverse axis y—y into an elongated pledget 78' having a generally cylindrical configuration. The pledget 78' has an insertion end 80', a trailing end 82' and a uniform cross-sectional area therebetween. The pledget 78' has a diameter $d_6$ that can range from between about 0.2 inches (about 5 mm) to about 2 inches (about 51 mm). Preferably, the diameter $d_6$ of the pledget 78' will be from about 0.5 inches (about 12.7 mm) to about 1 inch (about 25.4 mm). Most preferably, the diameter $d_6$ of the pledget 78' is less than about 0.75 inches (about 19 mm).

A withdrawal means 84, preferably in the form of an elongated string or ribbon is securely attached to the pledget 78'. The withdrawal string 84 will function as described above with reference to the first embodiment shown in FIGS. 3–6. The compressed pledget 78' with the withdrawal string 84 attached constitutes the finished urinary incontinence device 50'.

The insertion end 80' of the urinary incontinence device 50' is capable of expanding radially outward. It is the expansion in the radial direction that is the most important for this invention. Since the resilient member 52' is smaller in size than that depicted in the first embodiment shown in FIGS. 3–6, the amount of expansion will be less. The insertion end 80' can be designed to radially expand outward from between about 1.1 to about 4 times the initial diameter $d_6$ of the pledget 78'. Preferably, the insertion end 80' will be capable of radially expanding outward from between about 1.3 to about 3 times the initial diameter $d_6$ of the pledget 78'. More preferably, the insertion end 80' will be capable of radially expanding outward at least 1.4 times the diameter $d_6$ of the pledget 78'. The maximum amount of radial expansion of the insertion end 80' will depend on a number of factors, including the size, shape, location and composition of the resilient member 52', as well as the thickness and inherent properties of the non-absorbent 54 and the cover 70. It is envisioned that one could design the urinary incontinence device 50' such that the insertion end 80' could radially expand more than 2 times the initial diameter $d_6$ of the pledget 78', if desired.

Method

Figure 10:
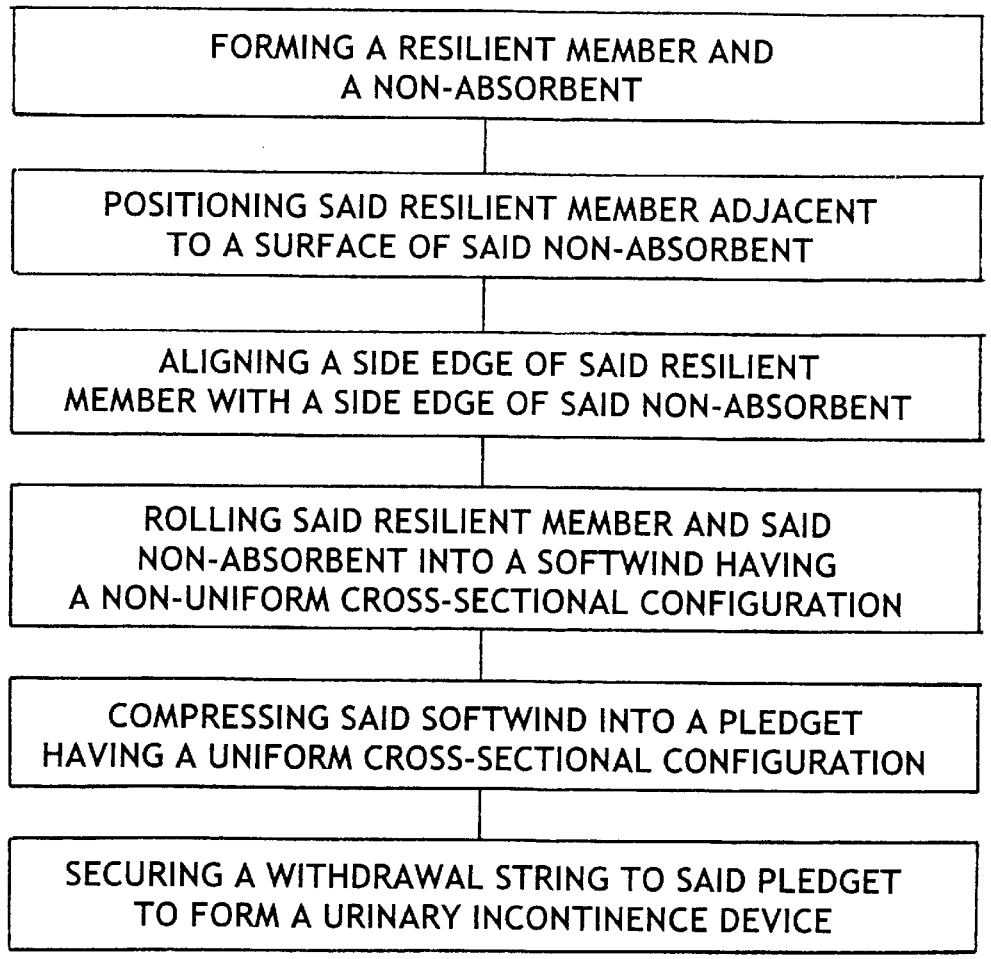
FIG. 10 is a flow diagram of a method of forming a urinary incontinence device.

The method of forming the urinary incontinence device 50 or 50' for alleviating female urinary incontinence, especially during episodes of increased intra-abdominal pressure will now be explained with reference to the flow diagrams shown in FIGS. 10 and 11. The method will be described with reference to the numerals denoted in FIG. 1, simply for ease of discussion, although it should be noted that the embodiment shown in FIG. 7 could also be utilized. The method includes the steps of forming a resilient member 52 into a desired geometrical shape. The forming step can be by shaping, cutting, slitting or assembling the resilient member 52 into a predetermined configuration. A preferred shape for the resilient member 52 is an elongated strip or rectangle although other shapes, such as a square, an oval, an elliptical shape, a racetrack profile, etc. would work. The resilient member 52 can be formed from twisted, curled or chemically cross-linked cellulose fibers or a mixture thereof. Alternatively, the resilient member 52 can be formed from polyvinyl alcohol or from polyethylene oxide.

The resilient member 52 should have a predetermined length $L_1$, a predetermined width $W_1$, and a predetermined thickness $T_1$. The dimensions of the length $L_1$, the width $W_1$, and the thickness $T_1$ can be varied to suit one's desired product. The resilient member 52 has a side edge 68 that is positioned on or adjacent to the side edge 64 of the non-absorbent 54. Preferably, the side edge 68 of the resilient member 52 is aligned so as to be coterminuous with the side edge 64 of the non-absorbent 54. In addition, the resilient member 52 is positioned adjacent to, and preferably in direct contact with, the first surface 56 of a non-absorbent 54 to form an assembly of two elements. Alternatively, an intermediate layer, such as one or more layers of tissue, can be placed therebetween, if desired.

The non-absorbent 54 is formed into a desired geometrical shape before the resilient member 52 is positioned adjacent to it. The non-absorbent 54 can be formed by cutting, shaping, slitting or assembling it into the desired configuration. A preferred configuration for the non-absorbent 54 is a rectangle, although other shapes, such as a square, an oval, an elliptical shape, a racetrack profile, etc. would work. The non-absorbent 54 has a predetermined length $L_2$, a predetermined width $W_2$ and a predetermined thickness $T_2$. The non-absorbent 54 has first and second surfaces, 56 and 58 respectively, which are spaced apart. The non-absorbent 54 also has a first longitudinal side edge 64 and a second longitudinal side edge 66. The non-absorbent 54 further has a central longitudinal axis x—x and a central transverse axis y—y. For best results, the resilient member 52 is aligned parallel to the central longitudinal axis x—x and is positioned such that its side edge 68 is coterminously aligned with the first longitudinal side edge 64 of the non-absorbent 54. The resilient member 52 can extend along the entire length $L_2$ of the non-absorbent 54 or only along a portion of the length $L_2$ of the non-absorbent 54. The resilient member 52 can have a length $L_1$ that ranges from between less than about 35% to about 100% of the length $L_2$ of the non-absorbent 54.

The resilient member 52 and the non-absorbent 54 are rolled up along the longitudinal axis x—x into an elongated softwind 72. The softwind 72 will have a first end 74, a second end 76 and a non-uniform cross-sectional area or configuration therebetween. When the side edge 68 of the resilient member 52 is aligned with the longitudinal side edge 64 of the non-absorbent 54, the resilient member 52 will be located adjacent to the second end 74 of the wound softwind 72. The softwind 72 can have a diameter at one end that is at least 1.2 times greater than the diameter of the other end. Alternatively, the softwind 72 can have a diameter at one end that is at least 1.4 times greater than the diameter of the other end. The softwind 72 is then be compressed into a pledget 78. The softwind 72 can be radially compressed to reduce its circumference or the softwind 72 can be compressed both radially as well as along its length. The pledget 78 has an insertion end 80, a trailing end 82 and a uniform cross-sectional area or configuration therebetween.

A withdrawal means 84, in the form of a string or ribbon, is secured to the pledget 78 to form a urinary incontinence device 50. Preferably, the withdrawal string 84 is securely connected to the pledget 78 approximate the trailing end 82. One way to accomplish this is to form an aperture 86 through the pledget 78 approximate the trailing end 82. The withdrawal string 84 is then passed through the aperture 86 and can be looped upon itself to form a secure connection. The finished urinary incontinence device 50 can be placed in a paper or plastic applicator 90 to facilitate insertion of the urinary incontinence device 50 into a woman's vagina 12. The applicator 90 can be telescopic in design using an inner tube and an outer tube. The urinary incontinence device 50 is housed in the outer tube and is dispensed into a woman's vagina 12 by pressing on the inner tube. As the inner tube moves into the outer tube, it causes the urinary incontinence device 50 to be expelled therefrom.

Alternatively, the urinary incontinence device 50 can be wrapped in a thermoplastic film to help retain its shape until ready for use. In this embodiment, the user would remove the wrapper and digitally insert the urinary incontinence device 50 into her vagina.

Referring again to FIGS. 3–5, it should be noted that the urinary incontinence device 50 could contain a cover 70. The cover 70 can have a length $L_3$ that is greater than the length $L_2$ of the non-absorbent 54. The cover 70 can also be treated with a surfactant to render it hydrophobic. When a cover 70 is utilized, the resilient member 52 and the non-absorbent 54 can be aligned and positioned on the cover 70 such that the non-absorbent 54 is adjacent to and preferably in direct contact with the cover 70. This means that the resilient member 52 will be spaced apart from the cover 70. All three layers, the resilient member 52, the non-absorbent 54 and the cover 70 can be rolled up together to form the elongated softwind 72. The entire softwind 72 will be radially compressed into the pledget 78.

While the invention has been described in conjunction with two specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

I claim:

1. A urinary incontinence device comprising:
   a) a resilient member; and
   b) a non-absorbent positioned adjacent to said resilient member, said non-absorbent being constructed from a fibrous material, said non-absorbent and said resilient member being rolled into a softwind having a first end, a second end, a first end diameter, and a second end diameter, said resilient member being located adjacent to said second end, said softwind having a second end diameter larger than said first end diameter, said softwind being radially compressed into a pledget having an initial diameter, an insertion end, a trailing end and a uniform cross-sectional area therebetween, wherein said insertion end is capable of expanding radially outward about 1.2 to about 10 times said initial diameter, said resilient member capable of expanding said insertion end of said pledget to provide a supportive backdrop for a woman's urethra when inserted into a woman's vagina.

2. The urinary incontinence device of claim 1 wherein said pledget has a uniform cross-sectional area extending between said insertion end and said trailing end, and after being positioned in a woman's vagina, said pledget exhibits a non-uniform cross-sectional area.

3. The urinary incontinence device of claim 1 wherein said resilient member is a closed cell foam.

4. The urinary incontinence device of claim 1 wherein said resilient member is an open cell foam.

5. The urinary incontinence device of claim 1 wherein said non-absorbent has a first side edge and a second side edge and said resilient member is positioned adjacent to said first side edge.

6. The urinary incontinence device of claim 5 wherein said resilient member is coterminuous with said first side edge of said non-absorbent.

7. The urinary incontinence device of claim 1 wherein said non-absorbent has a longitudinal axis and said resilient member is aligned parallel to said longitudinal axis.

8. The urinary incontinence device of claim 7 wherein said non-absorbent and said resilient member are rolled along said longitudinal axis to form said softwind having a non-uniform cross-sectional area.

9. The urinary incontinence device of claim 8 wherein said second end diameter of said softwind is at least 1.2 times said first end diameter.

10. A urinary incontinence device comprising:
    a) a resilient member;
    b) a non-absorbent positioned adjacent to said resilient member, said non-absorbent being constructed from a fibrous material, said non-absorbent and said resilient member being rolled into a softwind having a first end, a second end, a first end diameter, and a second end diameter, said resilient member being located adjacent to said second end, said softwind having a second end diameter larger than said first end diameter, said softwind being radially compressed into a pledget having an initial diameter, an insertion end, a trailing end and a uniform cross-sectional area therebetween, wherein said insertion end is capable of expanding radially outward about 1.2 to about 10 times said initial diameter, said resilient member capable of expanding said insertion end of said pledget to provide a supportive backdrop for a woman's urethra when inserted into a woman's vagina; and c) a withdrawal string secured to said pledget for facilitating removal of said urinary incontinence device from a woman's vagina.

11. The urinary incontinence device of claim 10 wherein an aperture is formed through said pledget approximate said trailing end and said withdrawal string passes through said aperture.

12. The urinary device of claim 10 wherein said second end diameter of said softwind is at least 1.4 times greater than said first end diameter.

13. The urinary incontinence device of claim 10 wherein said resilient member is formed from twisted, curled, or chemically cross-linked cellulose fibers or a mixture thereof.

14. The urinary incontinence device of claim 10 wherein said resilient member is formed from polyvinyl alcohol.

15. The urinary incontinence device of claim 10 wherein said resilient member is formed from polyethylene oxide.

16. A urinary incontinence device comprising:

a) a resilient member;

b) a non-absorbent positioned adjacent to said resilient member, said non-absorbent being constructed from a fibrous material, said non-absorbent and said resilient member being rolled into a softwind having a first end, a second end, a first end diameter, and a second end diameter, said resilient member being located adjacent to said second end, said softwind having a second end diameter larger than said first end diameter, said softwind being radially compressed into a pledget having an initial diameter, an insertion end, a trailing end and a uniform cross-sectional area therebetween, wherein said insertion end is capable of expanding radially outward about 1.2 to about 10 times said initial diameter, said resilient member capable of expanding said insertion end of said pledget to provide a supportive backdrop for a woman's urethra when inserted into a woman's vagina;

c) a cover at least partially enclosing said pledget; and d) a withdrawal string secured to said pledget for facilitating removal of said urinary incontinence device from a woman's vagina.

17. The urinary incontinence device of claim 16 wherein said cover is positioned adjacent to said non-absorbent and is located away from said resilient member.

18. The urinary incontinence device of claim 17 wherein said non-absorbent has a predetermined length and said cover has a length greater than the length of said non-absorbent.

19. The urinary incontinence device of claim 16 wherein said second end diameter of said softwind is at least 1.4 times said first end diameter.

20. The urinary incontinence device of claim 16 wherein said cover is treated with a surfactant to render it hydrophobic.

* * * * *